US00PP08520P

United States Patent [19]

Jessel, Jr.

[11] Patent Number: Plant 8,520

[45] Date of Patent: Dec. 28, 1993

[54] CARNATION PLANT NAMED CFPC TASKET

[75] Inventor: Walter H. Jessel, Jr., Salinas, Calif.

[73] Assignee: California Florida Plant Co., L.P., Salinas, Calif.

[21] Appl. No.: 16,651

[22] Filed: Feb. 8, 1993

[51] Int. Cl.[5] ..... A01H 5/00

[52] U.S. Cl. ..... Plt./70.7

[58] Field of Search ..... Plt./70.7

[56] References Cited

U.S. PATENT DOCUMENTS

P.P. 6,554 1/1989 Goldsberry ..... Plt. 70.7

P.P. 6,626 2/1989 Goldsberry ..... Plt. 70.7

*Primary Examiner*—James R. Feyrer

*Assistant Examiner*—Erich E. Veitenheimer

*Attorney, Agent, or Firm*—Christie, Parker & Hale

[57] ABSTRACT

A new carnation plant of low growth habit producing flowers of bright red coloration.

1 Drawing Sheet

BACKGROUND OF THE INVENTION

Unlike preceding pot carnations, i.e., Lilipots (Sakata), Rocky Mt. series (Goldsberry C.S.U.), and Knight Series (Goldsmith Seed Co.) CFPC Pot Carnations were selected and bred from indoor cut-types and are best grown under cover. The Lili-pots etc., were bred from outdoor garden-types and species and are best grown outdoors.

The CFPC pot varieties, such as 'CFPC Tasket' are dwarf due to a homozygous recessive dwarfing gene. If crossed to the aforementioned "pot-types", the resultant progeny returns to tall cut flower seedlings.

The Lili-pots and Knight series are seed crops. The Rocky Mt. and European pot varieties (cuttings) are no longer commercially available.

SUMMARY OF THE INVENTION

The present invention relates to a new and distinct variety of carnation plant which was discovered by me in a controlled planting as a sport of the cultivar 'CFPC Tisket'. It differs from its parent in flower coloring. Whereas 'CFPC Tasket' is bright red, flowers of its parent are light salmon pink and variegated salmon red. The varietal denomination of this new carnation is 'CFPC Tasket'.

Among the novel combination of characteristics possessed by the new variety which distinguishes it are dwarf plant growth habit, attractive flowers of light salmon pink variegated with salmon red coloring and suitability for growing as a pot plant in 4-inch pots.

'CFPC Tasket' is a product of a breeding program to produce stable cultivars with dwarf plant growth habit that do not require use of growth retardants to achieve the dwarf plant growth and which are also suitable for growing as potted plants. It is presently believed that this dwarf growth habit is due to a homozygous recessive dwarfing gene.

The new variety will produce flower buds that open well under moderate light conditions such as may occur in the home. 'CFPC Tasket' may tolerate temperatures as high as 120° F. and as low as 10° to 16° F. and therefore has a wide temperature tolerance range.

If planted outdoor, 'CFPC Tasket' will continue to recycle growth and blooms and may be perennial in nature, depending upon climate.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety depicted in color as nearly true as it is reasonably possible to make the same in a color illustration of this character. Although propagation by side shoot cuttings is described, other known methods of asexual reproduction may also be used to reproduce 'CFPC Tasket'.

DESCRIPTION OF THE NEW VARIETY

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate from the stated values depending upon varying environmental, seasonal and cultural conditions.

The new variety is one cultivar of a distinct type of true dwarf pot carnations, suitable for growing in 4" to 4½" pots (1 plant—1 pinch), and tolerant to temperatures of 10° F. to 120° F. No disease problems have been noted as yet. Keeping quality is generally 3 to 4 weeks. Flower buds will open from green buds to maturity with moderate light. 'CFPC Tasket' is distinct for its bright red flower color, durability and the combination of aforementioned traits. If planted outdoors, they will continue to recycle growth and blooms. For most sections of the country, they appear to be perennial in nature.

The information provided herein is based on observations of plants grown inside commercial greenhouses at Salinas, Calif. The height of plant and flower and foliage size are established as an average using standard commercial cultural practices.

Name: 'CFPC Tasket'.

Classification:

*Botanical.*—*Dianthus caryophyllus.*

*Commercial.*—Dwarf carnation, pot forcing type.

Parentage: Spontaneous sport of 'CFPC Tisket'.

PLANT

Height: About 6½ to 7½ inches from base of plant after one pinching.
Growing habit: Strong, semi-upright stems, free breaking.
Blooming habit: As a spray.
Blooming season: Year round.
Rooting time: About 13 days.
Disease resistance: Good.
Temperature tolerance: Wide range, 10° F.-16° F. to 120° F.
Breaking action: Good (average of five).

FOLIAGE

Color:
*Base.*—Near 141A (⅓-inch).
*Upper side.*—Near 141A.
*Lower side.*—Near 141B.
Size: About 3¾ inch long, thickness about 0.04 inch.
Quantity: Numerous.
Shape: Lanceolate.
Texture: Smooth.
Ribs: Central, keeled.
Arrangement: Bi-lateral along stem.
Stem color: Green.

BUD

Shape: Oval.
Color: Green.
Length: About ½-inch.
Diameter: About ¼-inch.

CALYX

Number of sepals: About 6.
Length: About ½-inch.
Width: About 1/5-inch.
Color:
*Outside.*—near to 144A.
*Inside.*—near to 144D.

BLOOM

Shape: Round.
Size:
*Diameter average.*—About 1½ inches.
*Depth average.*—About 1-inch.

Borne: As a spray, average about 58 buds and flowers per potted plant (4-inch).
Color:
*General tonality.*—Red.
*Upper side.*—Near to from 46B to 45C (faded).
*Lower side.*—Near 45C.
*Center.*—Near 46B.
*Outer petals.*—Near to from 46B to 45C (faded).
Keeping quality: About three to four weeks.
Fragrance: Very fragrant.

PETALS

Number: About 35.
Outer petals:
*Length.*—About ½-inch.
*Width.*—About ⅓-inch.
Central Petals:
*Length.*—About ⅓-inch.
*Width.*—About ¼-inch.
Texture: Smooth.
Form: Fan shaped.
Appearance: Shiny.

REPRODUCTIVE ORGANS

Stamens:
*Number.*—About 14.
*Arrangement.*—Around the ovary.
Anthers:
*Length.*—About 1/9-inch.
*Color.*—Near 159B.
Filaments:
*Length.*—About ¼-inch.
*Color.*—Near 155D.
Pistil:
*Number.*—About 2.
*Color.*—Near 155A.
*Length.*—About ⅓-inch.
Stigma:
*Number.*—About 2.
*Color.*—Near 155A.
Ovary:
*Shape.*—Conical.
*Color.*—Base — green. Apex — tan.
Fertility: Appears to be fertile as male, female.

I claim:

1. A new and distinct variety of true dwarf pot carnation plant, substantially as shown and described.

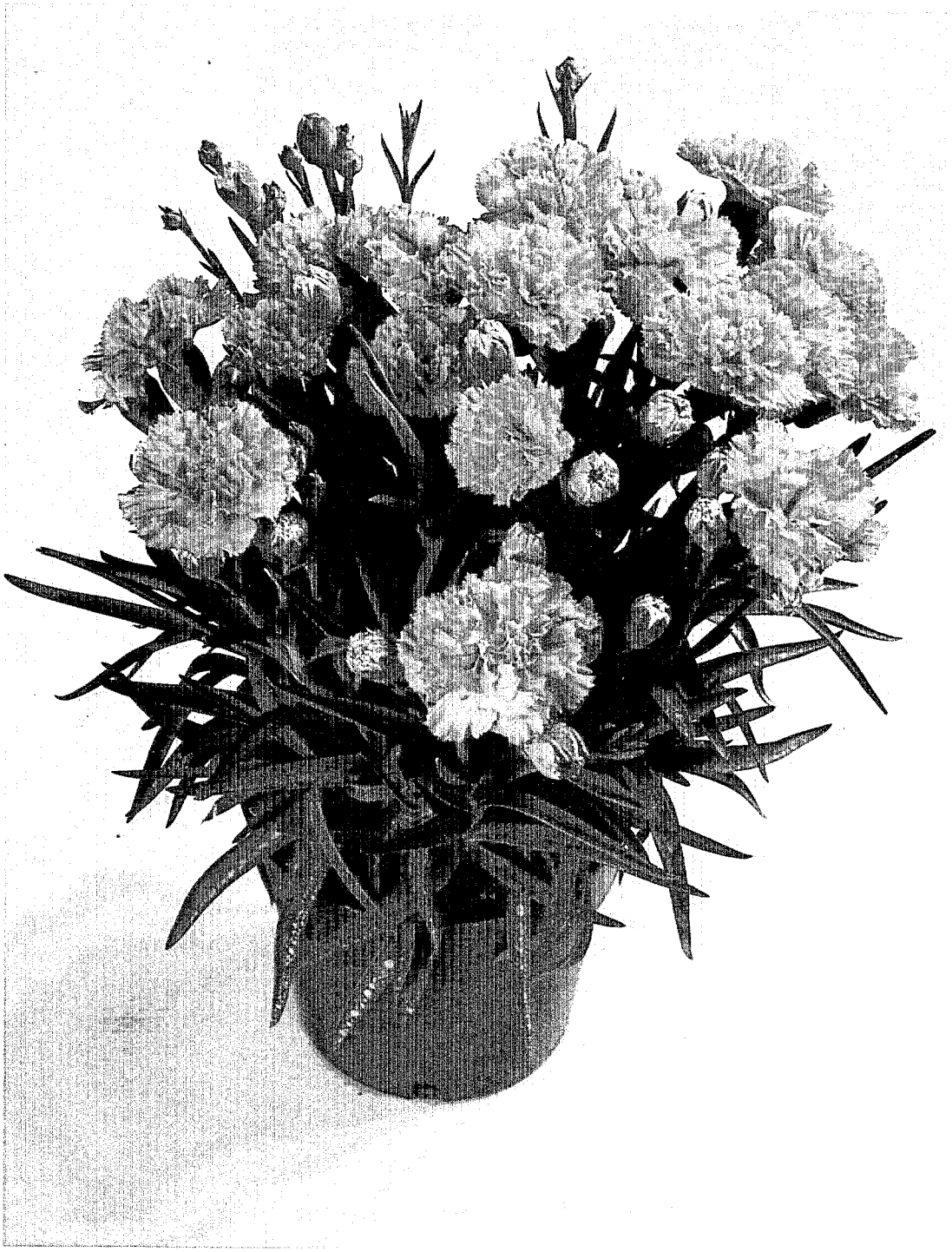

* * * * *